(12) United States Patent
Levisman

(10) Patent No.: US 6,315,564 B1
(45) Date of Patent: Nov. 13, 2001

(54) BONE IMPLANT

(76) Inventor: Ricardo Levisman, Aguero 1292-Lpiso, 1425 Ciudad de Buenos Aires (AR)

( * ) Notice: Subject to any disclaimer, the term of this patent is extended or adjusted under 35 U.S.C. 154(b) by 21 days.

(21) Appl. No.: 09/594,364

(22) Filed: Jun. 15, 2000

(30) Foreign Application Priority Data

Mar. 21, 2000 (AR) .............................................. P000101243

(51) Int. Cl.$^7$ .................................................. A61C 8/00
(52) U.S. Cl. ............................................. 433/174; 606/73
(58) Field of Search ................................... 433/174, 173; 606/73, 65

(56) References Cited

U.S. PATENT DOCUMENTS

| | | | |
|---|---|---|---|
| 4,103,422 | * | 8/1978 | Weiss et al. ........................... 433/174 |
| 4,348,183 | * | 9/1982 | Weissman ............................. 433/174 |
| 4,826,434 | * | 5/1989 | Krueger ................................ 433/174 |
| 5,061,181 | * | 10/1991 | Niznick ................................ 433/174 |

FOREIGN PATENT DOCUMENTS

377068 * 7/1990 (EP) ..................................... 433/174

* cited by examiner

*Primary Examiner*—Todd E. Manahan
(74) *Attorney, Agent, or Firm*—Greer, Burns & Crain, Ltd.

(57) ABSTRACT

An implant to be secured in a bone of a patient comprises an elongated body having an attachment portion to be inserted into the bone. The attachment portion includes a thread having a first cross-section dimension and a second cross-section dimension outwardly of the first dimension and larger than the first dimension.

22 Claims, 3 Drawing Sheets

BONE IMPLANT

BACKGROUND OF THE INVENTION

1. Field of the Invention

The present invention relates to bone implants and preferably to dental implants. More particularly, the invention relates to a bone implant that can be positively inserted and secured into the bone, preferably a jaw bone, by retention means provided in an elongated body of the implant. Even more preferably, the invention concerns a dental implant comprising a body to be secured within the jaw bone of a patient for receiving, after securement of the body in the bone, a dental prosthesis.

While specific reference to dental applications of the present implant will be made in the present disclosure and drawings, the bone implant of the invention is not restricted to dentistry but it may be applied to any other field where a prosthesis, a fixation device such as nail, etc. is to be secured into a bone. In addition, the term "patient" is applicable either to animals or human beings.

2. Description of the Prior Art

Bone implants, particularly dental implants, are well known in the dentistry field, many of them comprising a hollow or solid body to be secured into a bore within the bone. The body is adapted to be inserted in the socket of a tooth which has just been extracted so as to take the place of the removed tooth. The body must be retained within the socket without bridging or any other support from the adjacent or proximal teeth in the denture, and a prosthetic piece is then affixed in the body. To get a firm retention within the bone many retention means are provided in the body, always taking into consideration the benefits of the bone growth around the body and retention means. Most of the dental implants have looked for taking advantage of the bone growth to enhance the retentive function of the body in the bone. However, these known implants suffer from serious drawbacks. First, they fail to get a permanent retention and second, they are difficult to introduce into the bone.

To facilitate introduction of the implant into the bone, V-shaped threads are provided in most of the prior art implants. Generally, a bore is first drilled in the bone, preferably with a diameter lesser than the external diameter of the threads, which threads are designed to be self-tapping. However, this kind of threads is not reliable to get a proper retention of the implant in the bone. Implants are subjected to stresses and vibrations that resulting in loosening of the implants due to the lack of a reliable retention within the bone. This is due to a vectorial and rotational stresses appearing during chewing, biting, etc. and V-shaped threads, instead of proving retention, promotes the bone wearing and cracking.

It is well known in the art that a V-shaped thread transmits a 10 times greater shear force than a square thread design ("Implant Design Considerations for the Posterior Regions of the Mouth", Implant Dentistry, Vol. 8, Number 4, 1999), however, V-shaped threads are desired for tapping the bone and square threads only provide retention in the longitudinal or axial sense but no lateral retention is provided.

To overcome the above drawbacks several attempts have been made. U.S. Pat. No. 3,579,831, to Stevens et al., discloses a dental implant comprising a partially solid body including an external screw and a plurality of pins transversely passing through the body and extending into the bone jaw to provide an stabilization and anchoring result. This structure, however, needs of several components and the bone may be weakened by the insertion of multiple parts into the same, which components, like the pins, may also cause damages to adjacent teeth roots.

U.S. Pat. No. 3,708,883 to Flander, discloses an expandable dental implant comprising a body with a bottom portion having extensions which are spreadable for pressing the same against the bone, at a bore previously made in the bone. An expanding piece having a threaded shank is located into the body and a nut is threadably arranged in the shank. The nut may be rotated to cause the shank to lift and the expanding piece to spread the extensions of the body. The extensions are provided with external V-shaped threads or projections.

U.S. Pat. No. 6,008,431 to Caldarise, et al. discloses a bone prosthesis having a surface topography with recesses including a growth enhancement coating at the bottom of the recesses. The recesses have a depth of under three millimeters so that new bone growth spans the recesses and penetrates into the prosthesis over an extended surface textured region. While the dove-tail shaped recesses are already well know to enhance a rigid attachment and retention, the textured surface of Caldarise et al. does not provide threads necessary for screwing the implant into a bore in a bone or even for self tapping the bone.

U.S. Pat. No. 6,042,380 to De Rowe discloses an expandable dental implant designed to be inflated and deformed once in bore bone the patient to enhance retention, the implant including a deformable spiral tube which is wrapped around a central pin. The attachment thus is being improved by the deformation and shape of the tube but no screwing capability is provided.

It would be therefore convenient to have a bone implant capable of being easily inserted into a bone, preferably into a bore in the bone, and capable of being firmly attached in the bone with a permanent integration of the implant in the bone structure.

SUMMARY OF THE INVENTION

It is therefore an object of the present invention to provide a bone implant which can be easily installed in a bone structure and which is rapidly and firmly attached to the bone by integration with the bone structure.

It is still another object of the present invention to provide a dental implant which can be inserted into a bone jaw by self-drilling or self-tapping the wall of a bore in the bone.

It is a further object of the present invention to provide a bone implant, preferably a dental implant, that takes advantage of the benefits of cutting edges, preferably V-shaped threads, for introducing the implant into the bone without the drawbacks of conventional cutting threads that, when the implant is installed and the new bone growth has encircled the threads, produce a continuous cutting effect in surrounding bone.

It is even another object of the present invention to provide an implant to be secured in a bone of a patient, the implant comprising an elongated body having an attachment portion to be inserted into the bone, the attachment portion including at least one thread having a first cross-section dimension and a second cross-section dimension outwardly of the first dimension and larger than the first dimension, the second dimension forming a cutting edge for screwing the implant into the bone, and the difference between the dimension forming a retention of the implant into the bone.

It is even another object of the present invention to provide an implant to be secured into a bone of a patient, said implant comprising an elongated body having at least one attachment portion to be inserted into said bone, said at least one attachment portion including at least one thread outwardly radially projecting from the body, the thread having a cross-section defining, from inwardly to outwardly, at least a first dimension, a second dimension larger than the first dimension and a third dimension smaller than the second dimension.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 2:
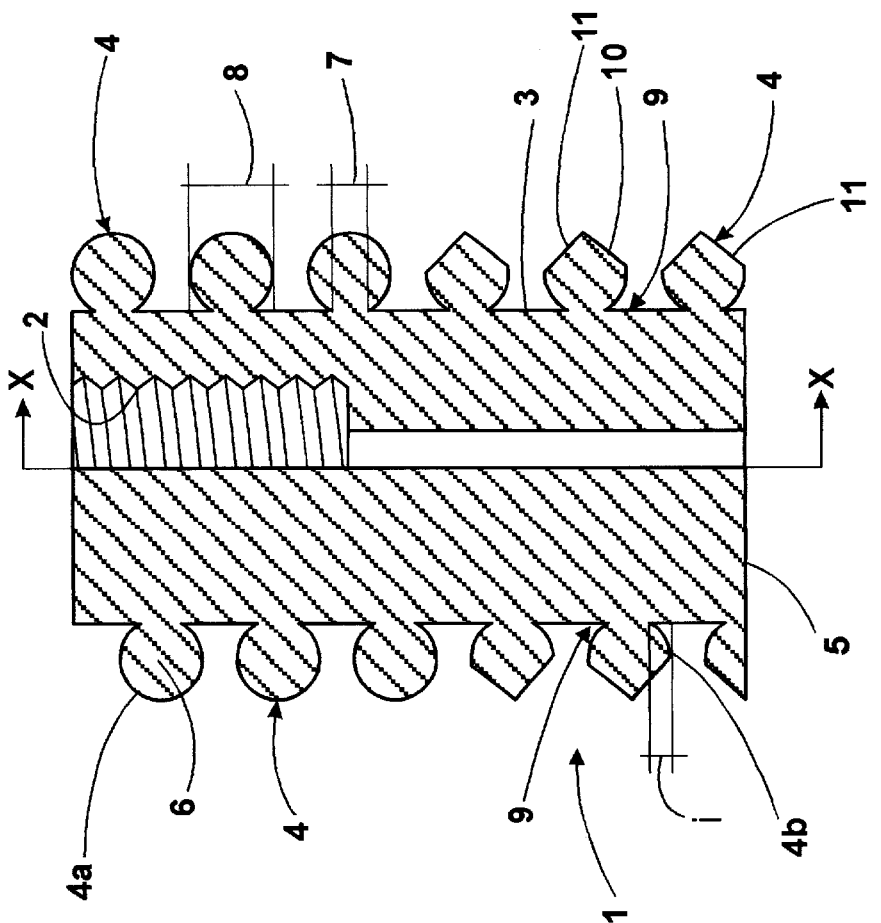
FIG. 2 shows a cross-sectional view taken through a plane containing a geometrical longitudinal axis of the implant of FIG. 1, with a half of the implant being shown as a solid implant and the other half shown as a hollow implant, for illustrative convenience.
Figure 1:
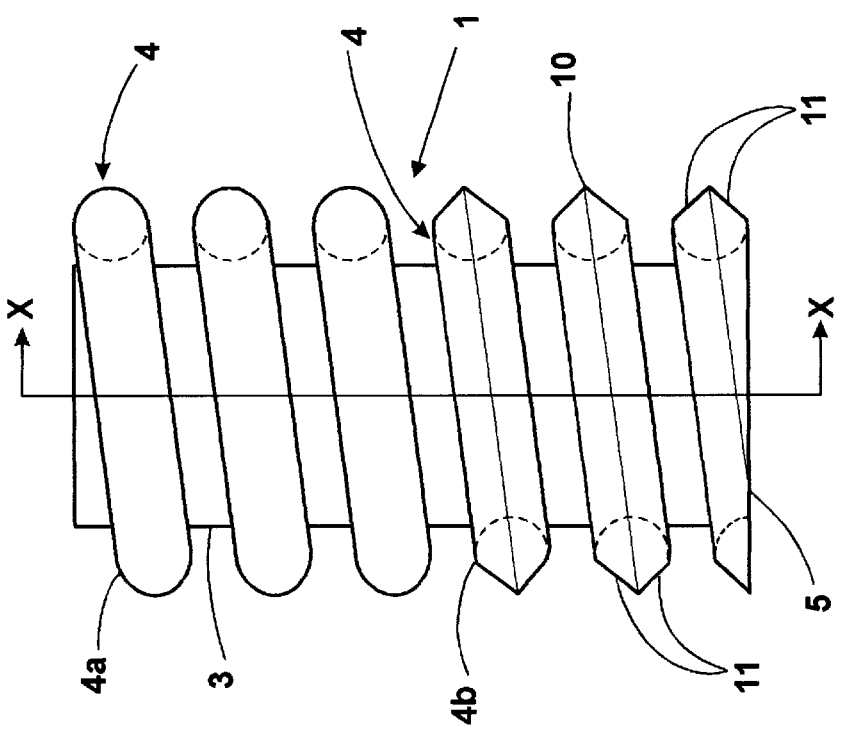
FIG. 1 shows a side elevation view of a dental implant according to the invention, illustrating two different thread shapes.

Now referring in detail to the drawings it may be seen from FIGS. 1 and 2, a first embodiment of the invention wherein the bone implant, more particularly a dental implant, comprises an elongated body generally indicated by reference 1. FIG. 1 shows a side view of the implant while FIG. 2 shows, in the same drawing, a solid body at the left side of the drawing, and a hollow body at the right side of the drawing. A body having a solid configuration may be used in several bone fixation applications, such as a nail fixation device to join two parts of a bone. For dental implants may be used a solid or a hollow body embodiment, like the one illustrated at the right side of FIG. 2, wherein a threaded inner bore 2 is provided to receive a tooth prosthesis not shown. For illustrative convenience both, the solid and hollow alternatives have been shown in FIG. 2, separated by a geometrical longitudinal axis X—X of the implant body. The cross-section depicted in FIG. 2 is taken through a plane containing axis X—X.

Body 1 may have a portion thereof not shown, designed to be out of the bone to receive an additional component of the complete implant, for example, a conventional artificial teeth. The part of the body shown in the Figures corresponds to an attachment portion 3 of the body and is designed to be secured within a bone of a patient. Attachment portion 3 includes at least one thread 4 helically extending around body 1 in order to define a helical thread and make the attachment portion to operate like a screw, preferably a self-tapping or self-drilling screw. While a helical thread has been illustrated, thread 4 may comprise one or more annular threads forming circles around attachment portion 2. Thread 4 can also comprise only one continuous thread or a plurality of threads or thread portions. In addition, threads 4 can all have the same radial extension or may be varied in order to tapper towards a bottom end 5 of body 1, thus providing the attachment portion with a cone-shaped configuration. This tapering alternative is shown in some of the remaining Figures to which reference will be made later.

According to the teachings of the invention attachment portion 3, depending on the kind of thread is being used, may be inserted into a bore in the bone, preferably, into the socket of a tooth that has been just extracted. Thread 4 has a cross-section 6 defining at least a first dimension 7 and a second dimension 8. Second dimension is larger than the first dimension and the second dimension is located radially outwardly relative the first dimension.

The inventive implant may combine threads with a section 6 entirely circular like the one illustrated in the first three threads 4a of FIGS. 1, 2, or partially circular, like the other bottom three threads 4b, the second dimension corresponds to the diameter of the circular section. According to the invention, the second dimension is larger than the first dimension in order to define at least one cavity to be filled with new bone growth. This cavity thus forms an interference i with the new bone growth which interference enhances the bone-implant integration and attachment. Any force transverse to axis X—X, a shear force for example, resulting from chewing and biting will act on the implant and will be transmitted to the bone. The retention provided by interference i will prevent the radial outermost surface of threads 4 acts against the bone, thus, if V-shaped threads are used, the sharp edge of the threads will not damage the bone.

Threads 4b in FIGS. 1 and 2 shows a radial outermost surface configuration comprising a sharp edge 10 formed in the circular thread section by plane lands 11 which may obtained by machining the threads after manufacturation of the same or during manufacturation or molding of threads 4b. In threads 4b, sharp edge 10 corresponds to a third dimension that is smaller than second dimension 8 and is radially outwardly located relative to second dimension 8. According to the invention, the three dimensions of the thread section are arranged from inwardly to outwardly in the following order, first dimension 7, second dimension 8 and third dimension corresponding to edge 10. Although edge 10 is a cutting edge for enhancing screwing of the implant into a bone bore, this edge will no cut the bone once the bone growth has filled the cavities formed around thread 4b by interference i.

Figure 3:
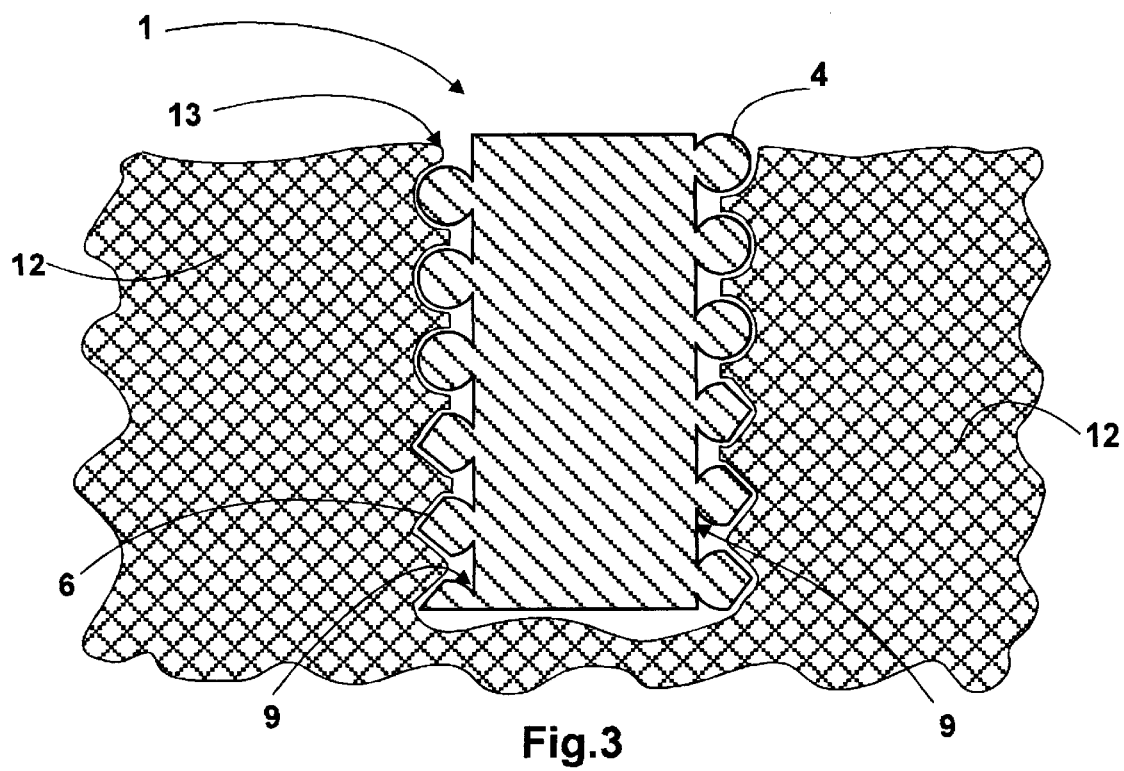
FIG. 3 shows a cross-sectional view of the implant of the invention located within a bore in a bone before the new bone growth has occurred.
Figure 4:
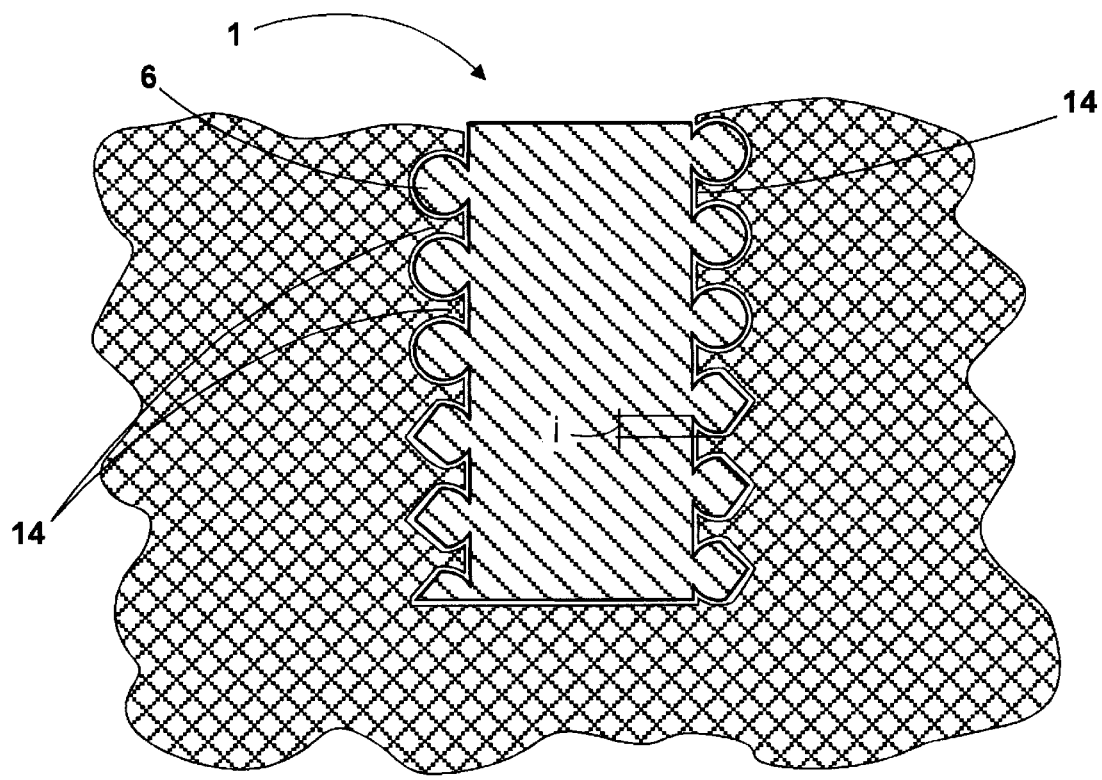
FIG. 4 shows a cross-section similar to FIG. 3 but with the new bone growth penetrated into the cavities between the threads in the implant.

FIGS. 3 and 4 shows an implant like the one of FIGS. 1, 2, but with threads 3 combined in order to have the entirely circular configuration of threads 4a and the configuration of threads 4b. All threads, however, may be like threads 4b. The fixation implant is secured within a jaw bone 12 and preferably within a bore 13 made in the bone. In the dentistry field bore 13 corresponds to the socket of tooth just extracted, which bore may be additionally drilled to prepare the same for receiving the implant. If applied to any medical field other than dentistry, bore 13 can be obtained by any drilling tool. It is preferably that implant 1 has an outer diameter larger than the diameter of the bore to get an initial retention. Thus, sharp edges 10 will cut and drill the bore wall and an enhanced initial retention will be provided. A final secure and positive attachment is achieved once the new bone growth 14 penetrates cavities 9 and each thread section 6 becomes attached and retained because it is entirely encircled by the bone growth 14. Thus, any lateral force, or shear force will be resisted by the locking interference i preventing the radial outermost surface of threads 4a, or sharp edges 10 of threads 4b from acting against the bone or, worst, penetrating into the bone. Without then thread section dimensions according to the invention, the shear forces would cause the implant to become loosened and the jaw bone probably extremely damaged.

Figures 5, 6:
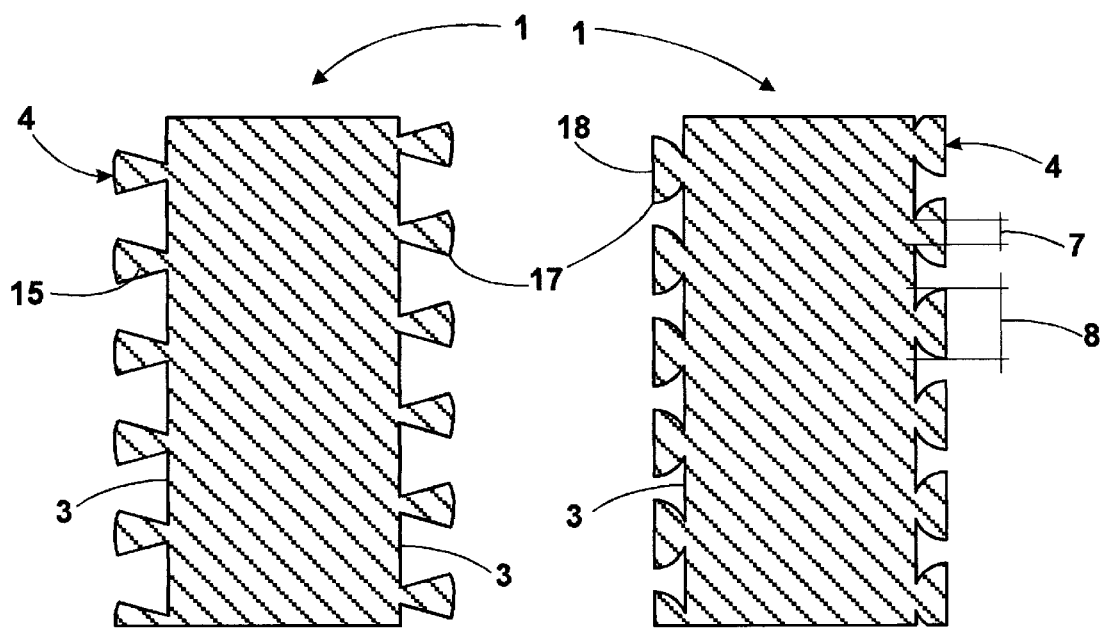
FIGS. 5–8 show side elevational, cross-sectional views of the implant of the invention with four different thread shapes.
Figures 7, 8:
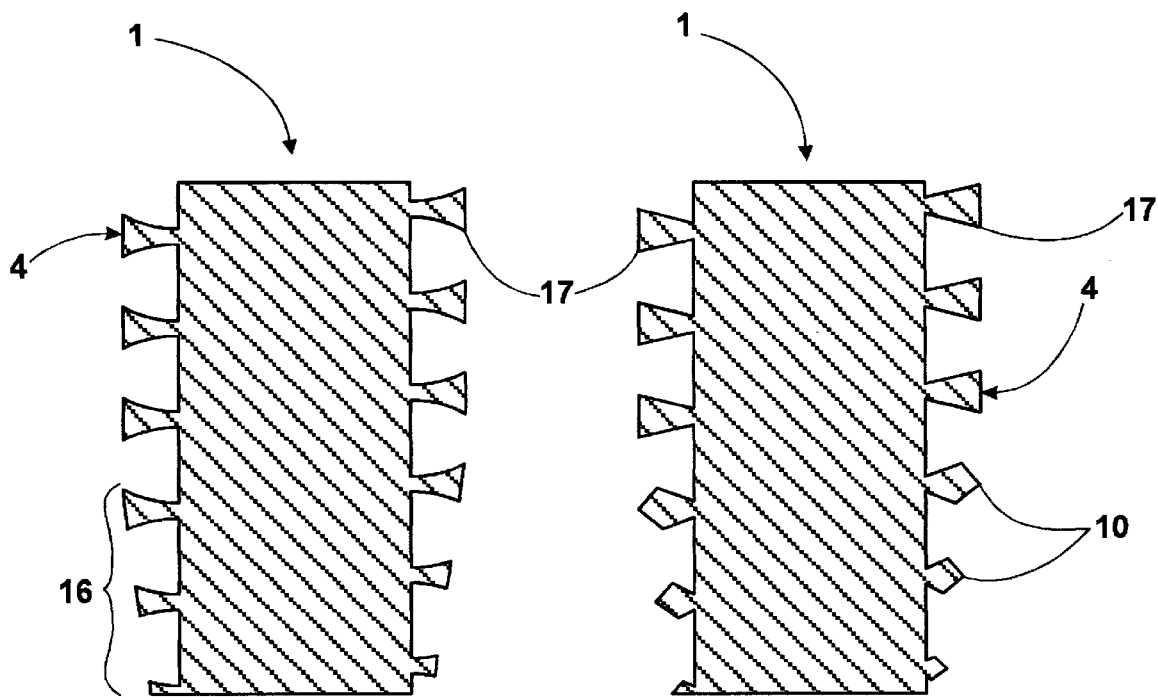

FIGS. 5–8 show different cross-sections for the threads according to the invention. Cross-sections in FIGS. 5–8 are all basically circular and triangular sections, each defined by a cut plane containing the longitudinal axis X—X of the implant body, the triangular sections being connected to the body through a vertex of the triangle, with a base of the triangle corresponding to the radially outermost surface of each thread 4. The threads in FIGS. 5–8 are all equivalent to the threads of FIGS. 1–4, therefore, they have been identified by the same reference number. Depending on the extent of connection between the thread and the body, the thread cross-section may be trapezoidal with the smallest base joined to the implant body. Therefore, the joining between the thread and the body may be understood like the vertex of a triangle or the small base of the trapezium. To provide the implant with the capability of being screwed into a bone, the radially outermost surface 18 of the threads are provided with a cutting edge 17. Edge 17 may operate like cutting edge 10 defined by the third dimension in FIGS. 1–4 and 8, however, cutting edge 17 is defined by the second dimension as illustrated in FIGS. 6–8. The second dimension in the threads depicted in FIG. 6 corresponds to the diameter of the semi-circular section, wherein the outermost surface 18 may be vertical or slightly inclined. The same concepts are applied to the triangular sections of FIGS. 5–7.

For illustrative purposes the three bottom threads in FIG. 8 have been illustrated with a third dimension corresponding to sharp edge indicated by number reference 10, like in FIGS. 1 and 2. First and second dimensions are indicated, in like manner, by references 7, 8, in FIG. 6. When including a sharp edge 10, threads have a rhomboidal cross-section with one of the vertex of the rhombus joined to the body. The sharp edge of the three bottom threads in FIG. 8 has been shown only in three threads as an example but edge 10 may be provided in all the threads. Thus, the three-dimension threads with cutting edges 10 may be combined with two-dimension threads with cutting edges 17. Of course, the implant may include only two-dimension threads with edges 17.

In addition to the foregoing, the radial extension of the threads, either two-dimension or three-dimension threads, can be tapered towards the bottom end of body 1 so as to give the attachment portion a cone configuration. While only part of the threads in FIG. 7 have been shown tapered all the threads may be shaped in this manner. For illustrative convenience only FIG. 7 includes tapered threads 16, however all the threads as illustrated in FIGS. 1–8 can be provided with tapered configuration.

The same above comments are applied to the provision of sharp edges for defining self-tapping threads, that is all the threads as illustrated in FIGS. 1–8 can be provided with edges for drilling and screwing purposes.

While preferred embodiments of the present invention have been illustrated and described, it will be obvious to those skilled in the art that various changes and modifications may be made therein without departing from the scope of the invention as defined in the appended claims.

I claim:

1. A implant to be secured into a bore provided in a bone of a patient, said implant comprising:

an elongated body having at least one attachment portion to be inserted within said bore, said at least one attachment portion including at least one thread outwardly radially projecting from the body, the thread having a cross-section defining at least a first dimension and a second dimension larger than the first dimension, the second dimension being outwardly radially located relative the first dimension, the second dimension forming a cutting edge for screwing the implant into the bone.

2. The implant of claim 1, wherein the body defines a geometrical longitudinal axis.

3. The implant of claim 2, wherein the thread cross-section is defined by a cut plane containing the longitudinal axis of the implant body, the cross-section being triangular with a vertex of the triangular section connected to the body.

4. The implant of claim 2, wherein the thread cross-section is defined by a cut plane containing the longitudinal axis of the implant body, the cross-section being circular.

5. The implant of claim 2, wherein the thread cross-section is defined by a cut plane containing the longitudinal axis of the implant body, the cross-section being trapezoidal with a smallest base of the trapezium section connected to the body.

6. The implant of claim 1, wherein the at least one thread helically extends around the body.

7. The implant of claim 1, wherein the at least one thread continuously extends around the body.

8. The implant of claim 1, wherein the first and second dimensions of the thread cross-section define at least one cavity to be filled with new bone growth.

9. The implant of claim 1, wherein the implant is a dental implant.

10. The implant of claim 1, wherein the at least one thread is radially tapered towards a bottom end of the body so that the attachment portion has at least a partial cone-shaped configuration tapered towards the bottom end of the implant body.

11. The implant of claim 1, further comprising at least one additional thread having a first cross-section dimension and a second cross-section dimension outwardly of the first dimension and larger than the first dimension.

12. A implant to be secured into a bone of a patient, said implant comprising:

an elongated body having at least one attachment portion to be inserted into said bone, said at least one attachment portion including at least one thread outwardly radially projecting from the body, the thread having a cross-section defining, from inwardly to outwardly, at least a first dimension, a second dimension larger than the first dimension and a third dimension smaller than the second dimension, the third dimension defining a sharp edge in the thread and the thread is a self-tapping thread.

13. The implant of claim 12, wherein the body defines a geometrical longitudinal axis.

14. The implant of claim 13, wherein the thread cross-section is defined by a cut plane containing the longitudinal axis of the implant body, the cross-section being rhomboidal with a vertex of the rhomboidal section connected to the body.

15. The implant of claim 13, wherein the thread cross-section is defined by a cut plane containing the longitudinal axis of the implant body, the cross-section being partially circular, with the first and second dimension being defined in the circular part of the cross-section.

16. The implant of claim 12, wherein the at least one thread helically extends around the body.

17. The implant of claim 12, wherein the at least one thread continuously extends around the body.

18. The implant of claim 12, wherein the first and second dimensions of the thread cross-section define at least one cavity to be filled with new bone growth.

19. The implant of claim 12, wherein the implant is a dental implant.

20. The implant of claim 12, wherein the attachment portion defines a screw.

21. The implant of claim 12, wherein the at least one thread is radially tapered towards a bottom end of the body so that the attachment portion has at least a partial cone-shaped configuration tapered to wards the bottom end of the implant body.

22. The implant of claim 10, further comprising at least one additional thread having a first cross-section dimension and a second cross-section dimension outwardly of the first dimension and larger than the first dimension.

\* \* \* \* \*